United States Patent
Hori et al.

Patent Number: 5,312,939
Date of Patent: May 17, 1994

[54] 2,2'-BIS (DICYCLOPENTYLPHOSPHINO)-1,1'-BINAPHTHYL AND TRANSITION METAL COMPLEX USING THE SAME AS LIGAND

[75] Inventors: Yoji Hori; Hidenori Kumobayashi, both of Tokyo, Japan

[73] Assignee: Takasago International Corporation, Tokyo, Japan

[21] Appl. No.: 727,709

[22] Filed: Jul. 10, 1991

[30] Foreign Application Priority Data

Jul. 12, 1990 [JP] Japan ................... 2-184535

[51] Int. Cl.$^5$ .................. C07F 15/04; C07F 15/00; C07F 9/02
[52] U.S. Cl. ..................... 556/14; 556/21; 556/136; 556/138; 568/17
[58] Field of Search ............ 556/14, 21, 136, 138; 568/17

[56] References Cited

U.S. PATENT DOCUMENTS

4,879,008 11/1989 Puckette ................. 204/72

OTHER PUBLICATIONS

Chemical Abstracts, vol. 111, No. 5, Abstract No. 39008u (1989).

Chemistry Letters, No. 7 (1985), pp. 1007–1008.

*Primary Examiner*—José G. Dees
*Assistant Examiner*—Porfirio Nazario
*Attorney, Agent, or Firm*—Sughrue, Mion, Zinn, Macpeak & Seas

[57] ABSTRACT

Novel 2,2'-bis(dicyclopentylphosphino)-1,1'-binaphthyl represented by formula (I):

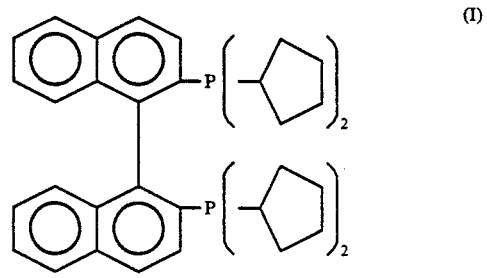

(I)

and a transition metal complex using the same as a ligand, are disclosed. The transition metal complex is industrially excellent as a catalyst for various asymmetric synthesis reactions.

12 Claims, No Drawings

2,2'-BIS(DICYCLOPENTYLPHOSPHINO)-1,1'-BINAPHTHYL AND TRANSITION METAL COMPLEX USING THE SAME AS LIGAND

FIELD OF THE INVENTION

This invention relates to a novel phosphine compound and, more particularly to a phosphine compound capable of forming a complex with a transition metal, e.g., rhodium, palladium, ruthenium, iridium, nickel, etc., to provide a catalyst useful in various asymmetric synthesis reactions.

BACKGROUND OF THE INVENTION

Many reports have been made on transition metal complexes such as, for example, catalysts useful for organic synthesis reactions, e.g., asymmetric hydrogenation, asymmetric isomerization, asymmetric silylation, etc. Among them, many of the complexes in which an optically active tertiary phosphine compound is coordinated to a transition metal, e.g., rhodium, palladium, ruthenium, iridium, nickel, etc., exhibit excellent performance as catalysts for asymmetric synthesis reactions. To further improve the performance of these catalysts, various phosphine compounds having a special structure have hitherto been developed as disclosed, e.g., in Chemical Society of Japan (ed. Kagaku Sosetsu, Vol. 32, pp. 237-238, "Yuki Kinzoku Sakutai no KagakuII" (1982). In particular, 2,2'-bis(diphenylphosphino 1,1'-binaphthyl (hereinafter abbreviated as BINAP) is one of the excellent phosphine ligands. Rhodium complexes and ruthenium complexes containing BINAP as a ligand have been reported in JP-A-55-61937 and JP-A-61-63690 (corresponding to U.S. Pat. No. 4,691,037 and European Patent 174,057), respectively (the term "JP-A" as used herein means an "unexamined published Japanese patent application"). Further, it has been reported that rhodium complexes and ruthenium complexes using 2,2'-bis[di(p-tolyl)phosphino]-1,1'-binaphthyl (hereinafter abbreviated as p-T-BINAP) as a ligand give satisfactory results in asymmetric hydrogenation and asymmetric isomerization as disclosed in JP-A-60-199898 (corresponding to U.S. Pat. No. 4,604,474 and European Patent 156,607) and JP-A-6163690, respectively. Furthermore, S. Inoue, et al. report in CHEMISTRY LETTERS, pp. 1007–1008 (1985) that asymmetric hydrogenation of nerol in the presence of, as a catalyst, a rhodium complex containing 2,2'-bis(dicyclohexylphosphino)1,1'-binaphthyl (hereinafter abbreviated as CYBINAP) gave citronellol having an optical purity of 66 %ee.

While a number of special phosphine compounds have been proposed in an attempt to provide complexes having improved performance as catalysts for asymmetric synthesis reactions as mentioned above, the conventional catalysts are still unsatisfactory in selectivity, conversion, and durability, depending on the type of the purposed reaction or reaction substrate. Hence, it has been demanded to develop a novel phosphine compound which provides a catalyst having markedly improved catalytic performance over the conventional ones.

SUMMARY OF THE INVENTION

In order to meet the above-described demand, the inventors have conducted extensive researches on various phosphine compounds. As a result, it has now been found that a transition metal complex using, as a ligand, a novel phosphine compound having a cyclopentyl group having introduced thereinto in place of the phenyl group of BINAP exhibits greatly improved selectivity and conversion in asymmetric syntheses as compared with complexes having BINAP, p-T-BINAP or CyBINAP as a ligand. The present invention has been completed based on this finding.

That is, the present invention relates to 2,2'-bis(dicyclopentylphosphino) -1,1'-binaphthyl (hereinafter abbreviated as CPBINAP) represented by formula (I):

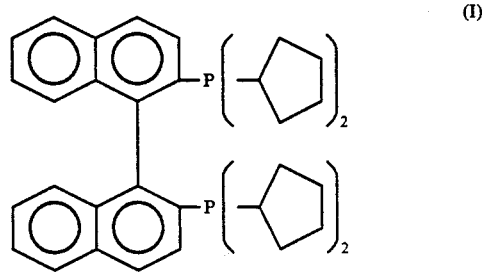

The present invention also relates to a novel transition metal complex using CPBINAP as a ligand.

DETAILED DESCRIPTION OF THE INVENTION

The compound of formula (I) includes and (+)-and (−)-optically active isomers, and the present invention embraces both of these isomers and a racemate thereof.

cPBINAP of formula (I) can be prepared through, for example, the following reaction schemes (A) and (B):

Reaction Scheme (A):

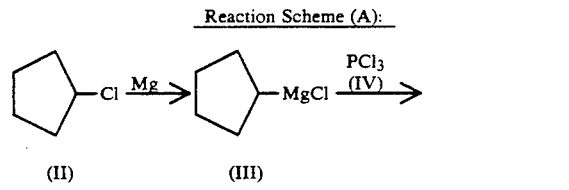

(II)    (III)

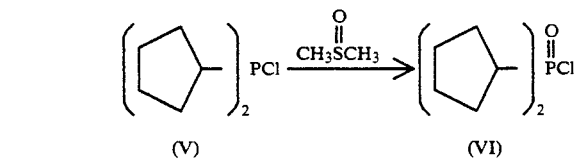

(V)    (VI)

Reaction Scheme (B):

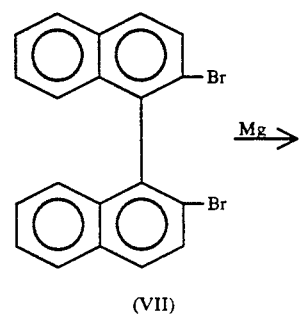

(VII)

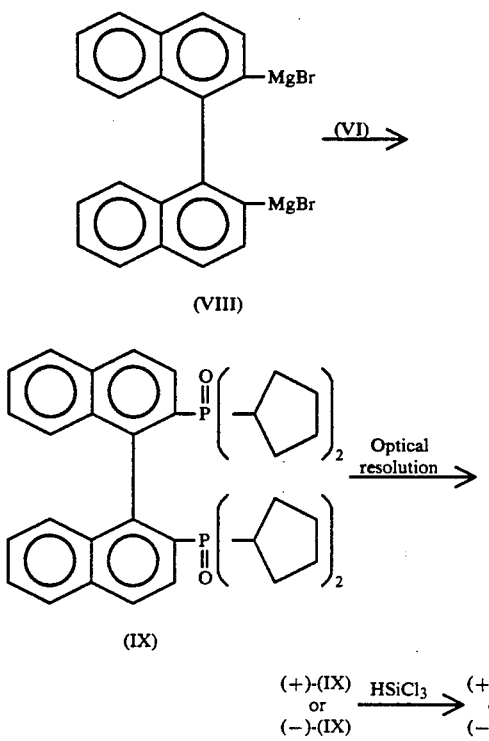

In reaction scheme (A), cyclopentyl chloride (II) is reacted with metallic magnesium to prepare a Grignard reagent (III), which is then condensed with phosphorus trichloride (IV) to obtain dicyclopentylphosphine chloride (V). The compound (V) is reacted with dimethyl sulfoxide. After the reaction, excess dimethyl sulfoxide and the solvent are removed by distillation under reduced pressure to obtain dicyclopentylphosphonyl chloride (VI).

In reaction scheme (B), 2,2′-dibromo-1,1′-binaphthyl (VII) obtained by the process disclosed in JP-A-55-61937 is reacted with metallic magnesium to prepare a Grignard reagent (VIII), which is then reacted with the above prepared compound (VI) to synthesize 2,2′-bis(-dicyclopentylphosphoryl)-1,1′binaphthyl (IX). The thus obtained racemic compound (IX) is dissolved in ethyl acetate while heating, an ethyl acetate solution of (+)-dibenzoyltartaric acid is added thereto, and the mixture is allowed to stand at room temperature for crystallization. The crystal is sampled in a small amount and suspended in chloroform. After adding 1N sodium hydroxide, the chloroform is removed by distillation to obtain a crude crystal of a (−)-isomer of the compound (IX). Optical rotation of the crude crystal is measured, and recrystallization from ethyl acetate and measurement of optical rotation on a sample are repeated until the measured optical rotation becomes constant. On obtaining a constant optical rotation value, the whole amount of the crystal is treated with 1N sodium hydroxide in chloroform in the same manner as described above to obtain a free (−)-isomer, phosphine oxide (−)-(IX).

Use of (−)-dibenzoyltartaric acid in place of the (+)dibenzoyltartaric acid in the above-described optical resolution yields a free (+)-isomer, phosphine oxide (+)-(IX).

The resulting (+)- or (−)-isomer of the compound (IX) is then reduced with trichlorosilane to obtain (+)- or (−)-cPBINAP (I) according to the present invention.

cPBINAP (I) according to the present invention forms a complex with a transition metal, e.g., rhodium, palladium, ruthenium, iridium, and nickel.

Specific examples of the transition metal complexes according to the present invention are shown below.

[Rh(COD)(cPBINAP)]ClO$_4$
   (wherein COD represents 1,5-cyclooctadiene, hereinafter the same)
Rh(COD)(cPBINAP)Cl
Rh(CO)Cl(cPBINAP)
PdCl$_2$(cPBINAP)
Ru$_2$Cl$_4$(cPBINAP)$_2$(NEt$_3$)
   (wherein Et represents an ethyl group, hereinafter the same)
[Ir(COD)(cPBINAP)]BF$_4$
[Ir(COD)(cPBINAP)]ClO$_4$
[Ir(COD)(cPBINAP)]PF$_6$
NiCl$_2$(cPBINAP)

The transition metal complexes of the present invention can be produced by, for example, the process for synthesizing [Rh(COD)(dppe)]ClO$_4$ (wherein dope represents 1,2-bis(diphenylphosphino)ethane) proposed by J. A. Osborn, et al. in *J. Am. Chem. Soc.*, Vol. 93, pp. 2397–2407 (1971). That is, [Ru(COD)-(cPBINAP)]ClO$_4$ is obtained by the reaction between [Rh (COD)$_2$]-ClO$_4$ and cPBINAP according to the present invention.

Rh(COD)(cPBINAP)Cl can be obtained by reacting commercially available [Rh(COD)Cl]$_2$ with cPBINAP according to the present invention in methylene chloride.

Rh(CO)Cl(cPBINAP) can be obtained by reacting commercially available [Rh(CO)$_2$Cl]$_2$ with cPBINAP according to the present invention in methylene chloride at room temperature according to the process for synthesizing Rh(CO)Cl(PPh$_3$)$_2$ (wherein Ph represents a phenyl group) as proposed by G. Wilkinson in *Inorg. Synth.*, Vol. 8, pp. 214–217 (1966).

Ru$_2$Cl$_4$(cPBINAP)$_2$(NEt$_3$) can be obtained by reacting [RuCl$_2$(COD)]$_n$, which is easily obtained by reacting ruthenium chloride and COD in an ethanolic solution, with CPBINAP according to the present invention by heating in a toluene solvent in the presence of triethylamine according to the process for synthesizing Ru$_2$Cl$_4$(BINAP)(NEt$_3$) disclosed in T. Ikariya, et al., *J. Chem. Soc., Chem. Commun.*, p. 922 (1985).

The thus obtained transition metal complex, when used as a catalyst for, for example, asymmetric hydrogenation of (E) -2- [(4-morpholinylcarbonyl)methyl]cinnamic acid, a starting material for synthesizing a renin inhibitor as reported in J. J. Plattner, et al., *J. Med. Chem.*, Vol. 31, pp. 2277–2288 (1988), or asymmetric hydrogenation of geraniol or nerol, exhibits high catalytic activity to produce reduction products of high optical purity in high optical yield. Further, a product having a desired absolute configuration can be obtained by appropriately selecting the absolute configuration of the compound (I), i.e., a (+)-isomer or a (−)-isomer, as a ligand for complex formation.

The present invention is now illustrated in greater detail with reference to Examples and Application Examples, but it should be understood that the present invention is not construed as being limited thereto. All the percents are by weight unless otherwise indicated.

Measuring instruments used in Examples are as follows.

| | |
|---|---|
| NMR: | Model AM-400 (400 MHz) manufactured by Bruker Inc.<br>Internal Standard:<br>$^1$H-NMR: tetramethylsilane<br>External Standard:<br>$^{31}$P-NMR: 85% phosphoric acid |
| Optical Rotation: | Model DIP-4 manufactured by JASCO Inc. |
| Optical Purity: | High-performance liquid chromatography by L-6000 (manufactured by Hitachi, Ltd.)<br>Detector: UV Detector L-4000 manufactured by Hitachi, Ltd. |
| Chemical Purity: | High-performance liquid chromatography by L-6000 (manufactured by Hitachi, Ltd.)<br>Detector: UV Detector L-4000 manufactured by Hitachi, Ltd. |

EXAMPLE 1

1) Preparation of Dicyclopentylphosphine Chloride (V)

In 500 ml of dehydrated diethyl ether, 73.05 g (0.699 mole) of cyclopentyl chloride was reacted with 17.28 g (0.72 mole) of metallic magnesium to prepare a Grignard reagent. The resulting Grignard reagent was added dropwise to a solution of 36.94 g (0.27 mole) of phosphorus trichloride in 200 ml of diethyl ether at −30° to −40 °C. The mixture was allowed to react at room temperature for 2 hours and then at 35° C. for 1 hours, followed by filtration. The filtrate was distilled under reduced pressure to obtain 31.25 g (0.1527 mole) of dicyclopentylphosphine chloride (V) in a yield of 56.5% (b.p. 105° C./3 mmHg).

2) Preparation of Dicyclopentylphosphonyl Chloride (VI)

A solution of 46.6 g (0.2284 mole) of dicyclopentylphosphine chloride obtained in (1) above in 100 ml of methylene chloride was cooled to −15° to −20° C., and 17.82 g (0.2284 mole) of dimethyl sulfoxide was added dropwise thereto over a period of 30 minutes. After waiting to room temperature, the reaction mixture was stirred for 2 hours, and the methylene chloride was removed by distillation under reduced pressure. The residue was dried at 80° C./3 mmhg for 3 hours to obtain 49.9 g (percent yield: 99.3%) of dicyclopentylphosphonyl chloride (VI) as a colorless solid.

3) Preparation of 2,2'-Bis(dicyclopentylphosphoryl)-1,1'-binaphthyl (IX)

2,2'-Dibromo-1,1'-binaphthyl, (48 g, 0.117 mole) was reacted with 7.0 g (0.29 mole) of metallic magnesium in 500 ml of toluene and 80 ml of tetrahydrofuran to prepare a Grignard reagent. To the resulting Grignard reagent was added dropwise a solution of 48 g (0.218 mole) of dicylopentylphosphonyl chloride obtained in (2) above in 250 ml of toluene at 0° C. over 1 hour, and the mixture was allowed to react at 60° to 800° C. for 4 hours. After adding thereto 100 ml of water at room temperature, the reaction mixture was stirred at 80° C. for 10 minutes, followed by liquid-liquid separation. The organic layer was concentrated, and the concentrate was purified by silica gel column chromatography using a 1:4 (by volume) mixture of acetone and hexane as a developing solvent to obtain 15.0 g (percent yield: 20.6%) of 2,2'-bis(dicyclopentylphosphoryl)-1,1'-binaphthyl (IX) as a colorless solid. The product was not liquefied on heating to 300° C. in melting point measurement.

| | |
|---|---|
| $^{31}$P-NMR (CD$_2$Cl$_2$) δ (ppm): | 46.9(s) |

4) Optical Resolution of 2,2'-Bis(dicyclopentylphosphoryl)1,1'-binaphthyl (IX):

In 2950 ml of ethyl acetate was dissolved 10.97 g (0.0176 mole) of the racemic 2,2'-bis(dicyclopentylphosphoryl)-1,1'-binaphthyl obtained in (3) above by heating at 70° C. to 80° C. A solution of 6.33 g (0.0176 mole) of (+)-dibenzoyltartaric acid in 50 ml of ethyl acetate was added thereto, and the solution was cooled to room temperature for crystallization, followed by filtration. A, small amount of the precipitate was sampled and suspended in chloroform, and a 1N sodium hydroxide aqueous solution was added thereto. The chloroform was removed by distillation to obtain a crude crystal of (−) -(IX) . The optical rotation of the crude crystal was measured, and the recrystallization from ethyl acetate, sampling, and measurement of optical rotation were repeated until the measured optical rotation became a constant value (hereinafter described) to finally obtain 7.79 g of a sparingly soluble diastereomer (opposite sign (−) (+) salt) . To the product were added 12 ml of a 1N sodium hydroxide aqueous solution and 350 ml of chloroform for neutralization, followed by stirring to thoroughly dissolve solid contents. After liquid-liquid Separation, the chloroform layer was washed three times with 700 ml portions of water. An adequate amount of sodium sulfate was added to the chloroform layer for drying, followed by filtration. The solvent was removed by distillation under reduced pressure, and the residue was recrystallized from 200 ml of ethyl acetate to obtain 4.5 g (0.00723 mole) of (−)-2,2'-bis(dicyclopentylphosphoryl)-1,1'-binaphthyl (−)-(IX) in a percent yield of 41.1% based on the racemate.

The same procedures as above were repeated, except for using (−)-dibenzoyltartaric acid in place of the (+)-dibenzoyltartaric acid, to obtain (30 )-2,2'-bis(dicyclopentylphosphoryl)-1,1'-binaphthyl (+)-(IX).

| | |
|---|---|
| (+)-Isomer $[\alpha]_D^{25}$: | +32.4° (c = 1.0, chloroform) |
| (−)-Isomer $[\alpha]_D^{25}$: | −30.8° (c = 1.0, chloroform) |

The optical purity of the (+)- and (−)-isomers was found to be 100% ee and 99.2% ee, respectively, as a result of high-performance liquid chromatography (hereinafter abbreviated as HPLC) under the following conditions.

| | |
|---|---|
| Column: | Chiral Cell OG (0.46 cm (d) × 25 cm (h)) manufactured by Daicel Chemical Industries, Ltd. |
| Developing Solvent: | Hexane:isopropanol = 95:5 (by volume) |
| Flow Rate: | 1 ml/min |
| UV Detection Wavelength: | UV-254 nm |

5) Preparation of (−)-cPBINA-P (−)-(I) and (+)-cPBINAP (+)-(I):

To 2.56 g (4.26 mmole) of the optically active compound obtained in (4) above, (−)-2,2'-bis(dicyclopentylphosphoryl)1,1'-binaphthyl (−)-(IX), were added 200 ml of xylene and 8.6 g (85.2 mmole) of triethylamine, and the mixture was stirred to form a solution. To the solution was added dropwise 11.4 g (85.2 mmole) of trichlorosilane over a period of 30 minutes, and the mixture was allowed to react at room temperature for 10 minutes, at 80° C. for 30 minutes, at 100° C. for 1 hour, at 120° C. for 1 hour, and finally at 130° C. overnight. After cooling to room temperature, 100 ml of a 3N sodium hydroxide aqueous solution was added thereto, and the mixture was stirred at 60° C. for 30 minutes, followed by liquid-liquid separation. The oily layer was washed with water and dried over magnesium sulfate. The solution was concentrated to about 3 ml under reduced pressure, and 20 ml of methanol was slowly added to the residue to obtain a crude reduction product. Recrystallization of the crude product from a 1:10 (by volume) mixture of toluene and methanol yielded 1.2 g (percent yield: 47.7%) of (-)-cPBINAP (−)-(I) as a colorless solid. Melting Point: 195°-197° C.

The same procedures were repeated, except for using optically active (+)-2,21-bis(dicyclopentylphosphoryl)-1,1'-binaphthyl (+)-(IX) obtained in (4) above in place of the (−)-2,2'-bis(dicyclopentylphosphoryl)-1,1'-binaphthyl (−)-(IX), to obtain 1.3 g (percent yield: 47.7%) of (+)-cPBINAP (+)-(I). Melting Point: 195°-197° C.

| | |
|---|---|
| (+)-Isomer: | $[\alpha]_D^{25}$ +24.5° (c = 0.51, chloroform) |
| (−)-Isomer: | $[\alpha]_D^{25}$ −23.9° (c = 0.66, chloroform) |
| $^1$H-NMR (CDCl$_3$) δ (ppm): | 0.70-2.45(m, 36H), 6.87(d, 2H, J=8.4Hz), 7.11(d-d-d, 2H, J=8.4, 6.8, 1.3Hz), 7.39 (d-d-d, 2H, J=8.2, 6.8, 1.1Hz), 7.84(d-d, 2H, J=8.5, 1.2Hz), 7.87(d, 2H, J=8.2Hz), 7.93(d, 2H, J=8.5Hz) |
| $^{31}$P-NMR (CD$_2$Cl$_2$) δ (ppm): | −14.2(s) |

EXAMPLE 2

Synthesis of [Rh(COD)((+)-cPBINAP)]ClO$_4$

In 1.0 ml of methylene chloride were dissolved 0.108 g (0.26 mmole) of [Rh(COD)$_2$]ClO$_4$ and 0.1658 g (0.28 mmole) of (+)-cPBINAP obtained in Example 1-(5), and the solution was allowed to react at room temperature for 3 hours. The reaction mixture was concentrated to 0.5 ml, and 2.0 ml of diethyl ether and 1.0 ml of hexane were added thereto to form a precipitate. The precipitate was collected by filtration and dried to obtain 0.231 g (percent yield: 85%) of the titled complex. Melting Point: 175°-190° C.

| | |
|---|---|
| $^{31}$P-NMR (CD$_2$Cl$_2$) δ (ppm): | 22.15(d, J=108.6Hz) |

EXAMPLE 3

Synthesis of [Rh(COD)((−)-cPBINAP)]BF$_4$

A mixture of 0.15 g (0.6 mmole) of [Rh(COD)Cl]$_2$, 0.360 g (0.6 mmole) of (−)-cPBINAP obtained in Example 1-(5), 0.200 g (1.8 nunole) of NaBF$_4$, 0.013 g (0.06 mmole) of (C$_2$H$_5$)$_4$NBr, 30 ml of methylene chloride, and 20 ml of water was allowed to react at 5° to 10° C. for 1.5 hours. The methylene chloride layer was separated and washed three times with 20 ml portions of water. The methylene chloride solution was concentrated to dryness to obtain 0.350 g (percent yield: 94.5%) of the titled complex. Melting Point: 230° C. with decomposition

| | |
|---|---|
| $^{31}$P-NMR (CD$_2$Cl$_2$) δ (ppm): | 12.15(d, J=176.7Hz) |
| | 31.19(d, J=122.2Hz) |

EXAMPLE 4

Synthesis of [Rh(COD)(+)-cPBINAP)]Cl

A mixture of [Rh(COD)Cl]$_2$ (0.0573 g, 0.233 mmole), 0.1374 g (0.233 mmole) of (+)-cPBINAP obtained in Example 1-5), and 10 ml of methylene chloride was reacted at 45° C. for 1 hour. After the reaction, the solvent was removed by distillation under reduced pressure to obtain 0.195 g (percent yield: 100%) of the titled complex.

| | |
|---|---|
| $^{31}$P-NMR (CD$_2$Cl$_2$) δ (ppm): | 46.55(d, J=230.6Hz) |
| | 64.13(d, J=192.6Hz) |

EXAMPLE 5

Synthesis of Rh(CO)Cl((+)-cPBINAP)

In 30 ml of methylene chloride were dissolved 29.0 mg (0.075 remole) of [Rh(CO)$_2$Cl]$_2$ and 88.4 g (0.15 remole) of (+)CPBINAP obtained in Example 1-(5), and the mixture was allowed to stand at room temperature for 30 minutes to conduct a reaction. The reaction mixture was concentrated to dryness to quantitatively obtain 113.6 mg of the titled complex. Melting Point: 220° C. with decomposition

| | |
|---|---|
| $^{31}$P-NMR (CD$_2$Cl$_2$) δ (ppm): | 16.65(d-d, J=123.9, 36.3Hz) |
| | 53.21(d-d, J=151.6, 36.3Hz) |

EXAMPLE 6

Synthesis of Ru$_2$Cl$_4$((+)-cPBINAP)$_2$(NEt$_3$)

A mixture of 0.082 g (0.289 mmole) of [RuCl$_2$.(COD)]$_n$, 0.207 g (0.352 mmole) of (+)-cPBINAP obtained in Example 1-(5), 0.23 g (2.27 mmole) of triethylamine, and 20 ml of toluene was stirred at 50° C. for 1 hour and then allowed to react at 110° C. for 10 hours. After the reaction, the solution was cooled to room temperature and concentrated to about 5 ml under reduced pressure. To the residue was added 5 ml of diethyl ether, and the thus formed precipitate was collected by filtration and dried at 40° C. under reduced pressure for 4 hours to obtain 0.24 g (percent yield: 84%) of the titled complex. The product was not liquefied on heating to 300° C. in melting point measurement.

| | |
|---|---|
| $^{31}$P-NMR (CD$_2$Cl$_2$) δ (ppm): | 46.73(s), 51.06(s) |

APPLICATION EXAMPLE 1

Asymmetric Hydrogenation of (E)-2-[(4-morpholinylcarbonyl)methyl]cinnamic Acid In a 100 ml stainless steel-made autoclave whose atmosphere had been displaced with nitrogen were charged 0.5 g (1.8 mmole) of (E)-2-[(4-morpholinylcarbonyl)methyl]cinnamic acid and 0.0162 g (0.018 nunole) of [Rh(COD)((+)-cPBINAP)]ClO$_4$ obtained in Example 6, and hydrogenation reaction was carried out at room temperature and at a hydrogen pressure of 5 kg/cm$^2$ for 20 hours. The reaction product was found to be (R)-2-[(4-morpholinylcarbonyl)methyl]-3-phenylpropionic acid.

The product was converted to its methyl ester by using diazomethane, and the ester was analyzed by HPLC under the following conditions. As a result, the conversion was 77.7%, and the optical yield was 76.4%ee.

| Column: | Chiral Cell OD (0.46 cm (d) × 25 cm (h)) manufactured by Daicel Chemical Industries, Ltd. |
| --- | --- |
| Developing Solvent: | Hexane:isopropanol = 9:1 (by volume) |
| Flow Rate: | 1 ml/min |
| UV Detection Wavelength: | UV-254 nm |

APPLICATION EXAMPLE 2

Asymmetric Hydrogenation of Nerol

In a 100 ml stainless steel-made autoclave whose atmosphere had been displaced with nitrogen were charged 1.54 g (10 mmole) of nerol, 0.0837 g (0.1 mmole) of Rh(COD)((+)-cBINAP)Cl obtained in Example 4, and 10 ml of benzene, and hydrogenation reaction was carried out at room temperature and at a hydrogen pressure of 30 kg/cm$^2$ for 17 hours. There was obtained 1.46 g of (S)-(-)-citronellol at a conversion of 99% and a selectivity of 99%. From the results of optical rotation $[\alpha]^{25}_D = -3.65°$ (c=10.1, chloroform), the optical yield was found to be 70%ee.

As described and demonstrated above, the novel phosphine compounds (I) according to the present invention form complexes with a transition metal, e.g., rhodium, palladium, ruthenium, iridium, nickel, etc., which are of great importance and of high value as a catalyst for various asymmetric synthesis reactions.

While the invention has been described in detail and with reference to specific embodiments thereof, it will be apparent to one skilled in the art that various changes and modifications can be made therein without departing from the spirit and scope thereof.

What is claimed is:

1. 2,2'-Bis(dicyclopentylphosphino)-1,1'-binaphthyl represented by formula (I):

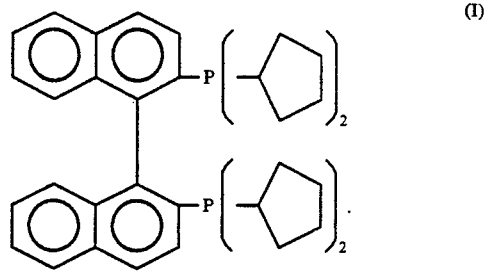

2. A metal complex comprising a transition metal and, as a ligand, 2,2'-bis(dicyclopentylphosphino)-1,1'-binaphthyl represented by formula (I):

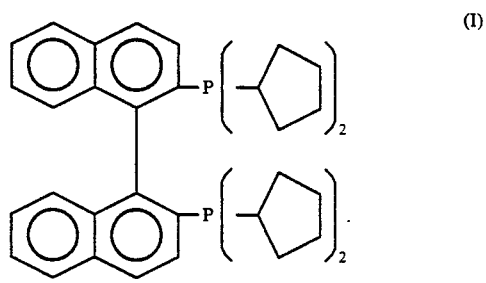

3. A metal complex as in claim 2, wherein said transition metal is rhodium, palladium, ruthenium, iridium, or nickel.

4. A metal complex as in claim 3, wherein said transition metal is rhodium or palladium.

5. (+)-2,2'-Bis(dicyclopentylphosphino)-1,1'-binaphthyl.

6. A metal complex comprising a transition metal and, as a ligand (+)-2,2'-bis(dicyclopentylphosphino)-1,1'-binaphthyl.

7. A metal complex as in claim 6, wherein said transition metal is rhodium, palladium, ruthenium, iridium, or nickel.

8. A metal complex as in claim 6, wherein said transition metal is rhodium or palladium.

9. (-)-2,2'-Bis(dicyclopentylphosphin)-1,1'-binaphthyl.

10. A metal complex comprising a transition metal and, as a ligand, (-)-2,2'-bis(dicyclopentylphosphino)-1,1'-binaphthyl.

11. A metal complex as in claim 10, wherein said transition metal is rhodium, palladium, ruthenium, iridium, or nickel.

12. A metal complex as in claim 10, wherein said transition metal is rhodium or palladium.

* * * * *